US009839449B2

(12) United States Patent
Abitbol et al.

(10) Patent No.: US 9,839,449 B2
(45) Date of Patent: Dec. 12, 2017

(54) TRANSLATIONAL PLATE AND COMPRESSOR INSTRUMENT

(71) Applicant: K2M, Inc., Leesburg, VA (US)

(72) Inventors: Jean Jacques Abitbol, Del Mar, CA (US); Gordon Donald, Red Bank, NJ (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/430,660

(22) Filed: Feb. 13, 2017

(65) Prior Publication Data
US 2017/0150998 A1 Jun. 1, 2017

Related U.S. Application Data

(62) Division of application No. 14/334,991, filed on Jul. 18, 2014, now Pat. No. 9,579,128.

(60) Provisional application No. 61/856,265, filed on Jul. 19, 2013.

(51) Int. Cl.
*A61B 17/80* (2006.01)
*A61B 17/70* (2006.01)

(52) U.S. Cl.
CPC ........ *A61B 17/7059* (2013.01); *A61B 17/808* (2013.01); *A61B 17/8009* (2013.01); *A61B 17/8019* (2013.01); *A61B 17/8023* (2013.01)

(58) Field of Classification Search
CPC .................................................... A61B 17/88
See application file for complete search history.

(56) References Cited

U.S. PATENT DOCUMENTS

| | | |
|---|---|---|
| 3,386,437 A | 6/1968 | Treace |
| 3,426,364 A | 2/1969 | Lumb |
| 4,422,451 A | 12/1983 | Kalamchi |
| 5,484,439 A | 1/1996 | Olson et al. |
| 5,616,142 A | 4/1997 | Yuan et al. |
| 5,681,312 A | 10/1997 | Yuan et al. |
| 5,713,900 A | 2/1998 | Benzel et al. |
| 5,843,082 A | 12/1998 | Yuan et al. |
| 6,322,562 B1 | 11/2001 | Wolter |
| 6,402,756 B1 | 6/2002 | Ralph et al. |
| 6,503,250 B2 | 1/2003 | Paul |
| 6,551,316 B1 | 4/2003 | Rinner et al. |
| 6,623,486 B1 | 9/2003 | Weaver et al. |
| 6,932,820 B2 | 8/2005 | Osman |
| 7,186,254 B2 | 3/2007 | Dinh et al. |
| 7,186,256 B2 | 3/2007 | Michelson |
| 7,273,481 B2 | 9/2007 | Lombardo et al. |
| 7,291,152 B2 | 11/2007 | Abdou |

(Continued)

*Primary Examiner* — Nicholas Plionis
(74) *Attorney, Agent, or Firm* — Carter, DeLuca, Farrell & Schmidt, LLP

(57) ABSTRACT

A bone plate that is configured to operatively attach to bone includes a first segment, a second segment, and a locking mechanism. The first segment includes a compression notch. The first and second segments are positioned along a longitudinal axis and are movable relative to one another. The locking mechanism inhibits relative axial movement of the first and second segments along the longitudinal axis away from one another. The locking mechanism includes first and second grooves disposed on the second segment. The first and second grooves and the compression slot are configured to receive an instrument to move the first segment towards the second segment along the longitudinal axis.

16 Claims, 15 Drawing Sheets

(56) References Cited

U.S. PATENT DOCUMENTS

| | | |
|---|---|---|
| 7,303,564 B2 | 12/2007 | Freid et al. |
| 7,306,605 B2 | 12/2007 | Ross |
| 7,318,825 B2 | 1/2008 | Butler et al. |
| 7,331,961 B2 | 2/2008 | Abdou |
| 7,341,590 B2 | 3/2008 | Ferree |
| 7,344,537 B1 | 3/2008 | Mueller |
| 7,479,143 B2 | 1/2009 | Suh et al. |
| 7,621,914 B2 | 11/2009 | Ralph et al. |
| 7,641,675 B2 | 1/2010 | Lindemann et al. |
| 8,449,585 B2 | 5/2013 | Wallenstein et al. |
| 8,636,738 B2 | 1/2014 | McClintock et al. |
| 9,579,128 B2 | 2/2017 | Abitbol et al. |
| 2002/0052605 A1 | 5/2002 | Grooms et al. |
| 2002/0183755 A1 | 12/2002 | Michelson |
| 2003/0130661 A1* | 7/2003 | Osman ............... A61B 17/7059 606/71 |
| 2004/0015172 A1 | 1/2004 | Biedermann et al. |
| 2004/0204712 A1 | 10/2004 | Kolb et al. |
| 2005/0043732 A1 | 2/2005 | Dalton |
| 2005/0137597 A1 | 6/2005 | Butler et al. |
| 2005/0177163 A1 | 8/2005 | Abdou |
| 2006/0009845 A1 | 1/2006 | Chin |
| 2006/0116683 A1 | 6/2006 | Barrall et al. |
| 2006/0200134 A1 | 9/2006 | Freid et al. |
| 2006/0235398 A1 | 10/2006 | Farris et al. |
| 2006/0235405 A1 | 10/2006 | Hawkes |
| 2007/0123881 A1 | 5/2007 | Ralph et al. |
| 2007/0233117 A1 | 10/2007 | Butler et al. |
| 2007/0255409 A1 | 11/2007 | Dickson et al. |
| 2008/0065070 A1 | 3/2008 | Freid et al. |
| 2008/0108998 A1 | 5/2008 | Lindemann |
| 2008/0154312 A1 | 6/2008 | Colleran et al. |
| 2008/0161854 A1 | 7/2008 | Bae et al. |
| 2008/0234680 A1 | 9/2008 | Zaiser et al. |
| 2008/0234681 A1 | 9/2008 | Baynham |
| 2008/0269753 A1 | 10/2008 | Cannestra |
| 2009/0043341 A1 | 2/2009 | Tyber et al. |
| 2009/0076509 A1 | 3/2009 | Bush, Jr. et al. |
| 2009/0088807 A1 | 4/2009 | Castaneda et al. |
| 2010/0082029 A1* | 4/2010 | Ibrahim ............. A61B 17/7059 606/71 |
| 2010/0331849 A1 | 12/2010 | Riesinger et al. |
| 2011/0106172 A1 | 5/2011 | Wallenstein et al. |
| 2011/0319939 A1 | 12/2011 | Kretzer et al. |
| 2012/0083846 A1* | 4/2012 | Wallenstein ....... A61B 17/7059 606/279 |
| 2014/0128873 A1 | 5/2014 | McClintock et al. |

* cited by examiner

TRANSLATIONAL PLATE AND COMPRESSOR INSTRUMENT

CROSS-REFERENCE TO RELATED APPLICATIONS

This application is a divisional of U.S. patent application Ser. No. 14/334,991, filed Jul. 18, 2014, which claims the benefit of, and priority to, U.S. Provisional Application Ser. No. 61/856,265, filed Jul. 19, 2013. The entire contents of each of the above applications are hereby incorporated herein by reference.

BACKGROUND

1. Technical Field

The present disclosure relates to a device and instrument for use in orthopedic surgeries and, more specifically, to a plate that is attachable to the vertebrae that is configured to compress during the procedure and an instrument configured to engage the plate to compress the plate.

2. Discussion of Related Art

The human spinal column is a highly complex structure. It includes twenty-four discrete bones, known as vertebrae, coupled sequentially to one another to house and protect critical elements of the nervous system. The cervical portion of the spine, which includes the neck of the spine up to the base of the skull, includes the first seven vertebrae.

For many reasons, such as aging and trauma, the intervertebral discs can begin to deteriorate and weaken. This may result in chronic pain, degenerative disc disease, or even tearing of the disc. Ultimately, the disc may deteriorate or weaken to the point of tearing and herniation, in which the inner portions of the disc protrude through the tear. A herniated disc may press against or pinch the spinal nerves, thereby causing radiating pain, numbness, and/or diminished strength or range of motion.

Many treatments are available to remedy these conditions, including surgical procedures in which one or more damaged intervertebral discs are removed and replaced with a prosthetic. However, should the prosthetic protrude from between the adjacent vertebrae and contact the surrounding nerves or tissues, the patient may experience additional discomfort. In procedures for remedying this problem, a spinal plate is affixed to the vertebrae and oriented to minimize such protrusion. In addition, the plate provides fixation and support to maintain spinal stability while the fusion occurs.

Spinal plates and cervical plates in particular, are known in the art. Fixed cervical plates generally exhibit unalterable, static dimensions. During the natural subsidence of the spinal column after surgery, the overall length of the spinal column gradually decreases. Fixed cervical plates resist this change due to their fixed axial length, which may eventually stress the spine and cause pain or discomfort. Adjustable cervical plates attend to this predicament by providing a mechanism through which the plate is shortened to accommodate for a measure of subsidence. However, some adjustable plates require subsequent surgical procedures to adjust the axial dimensions of the plate. In addition to accommodating subsidence, it is critical for the plate to provide means to apply constant loading of an implant placed between adjacent vertebrae in order to promote fusion.

SUMMARY

In an aspect of the present disclosure, a bone plate that is operatively attachable to bone includes a first segment, a second segment, and a locking mechanism. The first segment includes a compression notch. The first and second segments are positioned along a longitudinal axis and are movable relative to one another. The locking mechanism inhibits relative axial movement of the first and second segments away from one another along the longitudinal axis. The locking mechanism includes first and second grooves disposed on the second segment. The first and second grooves and the compression slot are configured to receive an instrument to move the first segment towards the second segment along the longitudinal axis. The locking mechanism can be releasable to permit axial movement of the first and second segments apart from one another. The locking mechanism can include a tongue that extends from the first segment. The tongue operatively engages the first and second grooves to sequentially and releasably lock the first and second segments to inhibit axial movement of the first and second segments apart from one another while enabling axial movement of the first and second segments towards one another. The first and second segments are attachable to vertebral bodies such that the first and second segments move toward one another in response to the subsidence of the vertebral bodies. The first and second segments can include screw holes that receive screws. The locking mechanism can include a third and fourth groove disposed on the second segment. Each of the grooves can be spaced apart at a length along the longitudinal axis from another groove. The compression notch may be placed at a lateral mid-point of the first segment.

According to another aspect of the present disclosure, a surgical system includes a bone plate and a compression instrument. The bone plate includes a first segment having a compression notch, a second segment, and a locking mechanism that includes first and second grooves disposed on the second segment. The compression instrument includes a handle, a first tip, and a second tip. The first tip is sized and configured to engage one of the first and second grooves of the locking mechanism. The second tip is sized and configured to engage the compression notch. The first and second tips are movable relative to one another. The first and second tips are configured to move the first segment towards the second segment along the longitudinal axis when engaged with one of the first and second grooves and the compression slot. A tongue of the locking mechanism can include a tab that is configured to operatively engage the first and second grooves to sequentially and releasably lock the first and second segments. The first tip of the compression instrument can be configured to disengage the tab of the locking mechanism from the first and second grooves. The locking mechanism can be releasable to permit axial movement of the first and second segments apart from one another. The system can further include a spacer positioned between the first and second segment of the bone plate. The spacer can be configured to maintain a predefined space between the first and second segments.

According to yet another aspect of the present disclosure, a method of attaching a bone plate to vertebrae includes providing a bone plate, securing a first segment of the bone plate to a first vertebra with a first bone screw inserted through a first screw hole, securing a second segment of the bone plate to a second vertebra with a second bone screw inserted through a second screw hole, and compressing the first segment towards the second segment of the bone plate. Compressing the first segment of the bone plate towards the second segment of the bone plate includes compressing a handle of a compression instrument while a first tip of the compression instrument engages one of first and second grooves and a second tip of the compression instrument engages a compression notch. The method can include removing a spacer from between the first and second segments before compressing the first segment of the bone plate towards the second segment of the bone plate.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
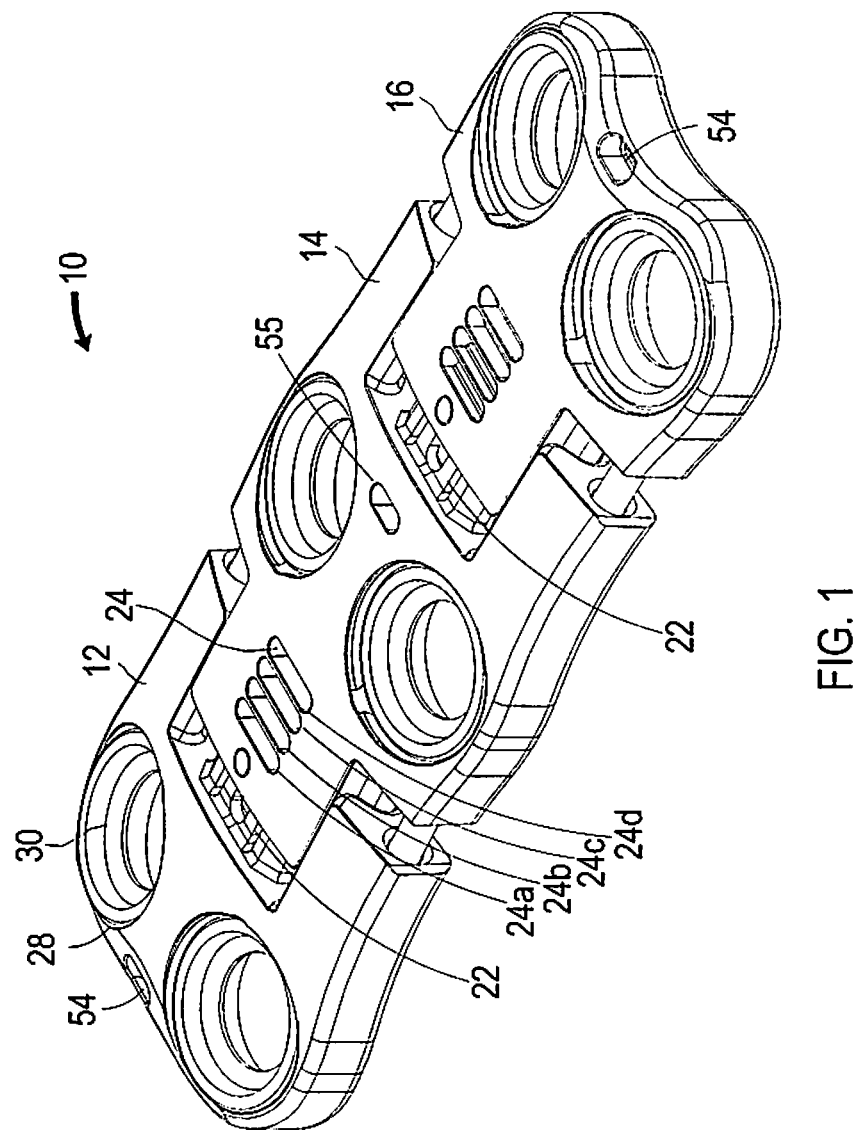
FIG. 1 is a perspective view of an exemplary embodiment of a translational plate in accordance with the present disclosure including three segments.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "medial" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

A translational plate 10 that allows for adjustment over a specified range, while maintaining the strength and functionality of plate 10, will now be described with reference to FIGS. 1-8. Plate 10 may generally be operatively coupled to a patient's spine, and in particular to the cervical vertebrae, i.e., the vertebrae in the patient's neck. Plate 10 includes a plurality of adjacent segments that are axially movable relative to one another. The number of segments that plate 10 includes corresponds to the number of vertebral levels plate 10 is to bridge. As shown in FIGS. 1 and 2-8, plate 10 includes three segments 12, 14, 16. As shown in FIG. 1A, a translational plate 10a includes two segments 12, 16. It is also contemplated that the translational plate may include more than three segments.

Figure 1A:
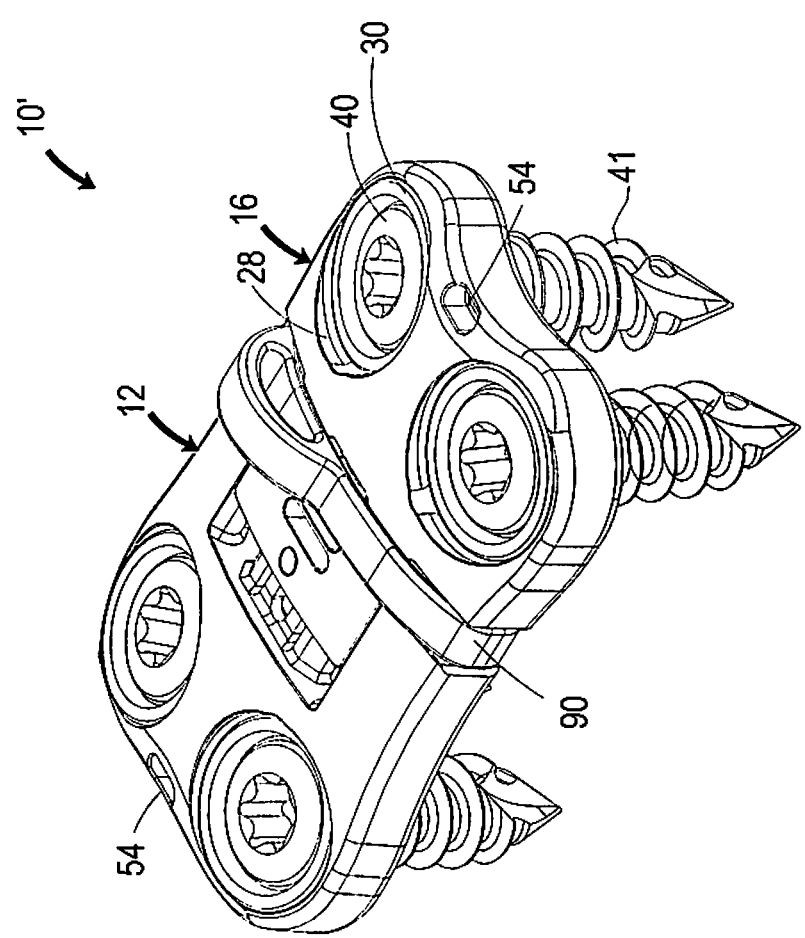
FIG. 1A is a perspective view of another exemplary embodiment of a translational plate in accordance with the present disclosure including two segments with bone screws inserted through the screw holes and spacers positioned between the segments.
Figure 2:
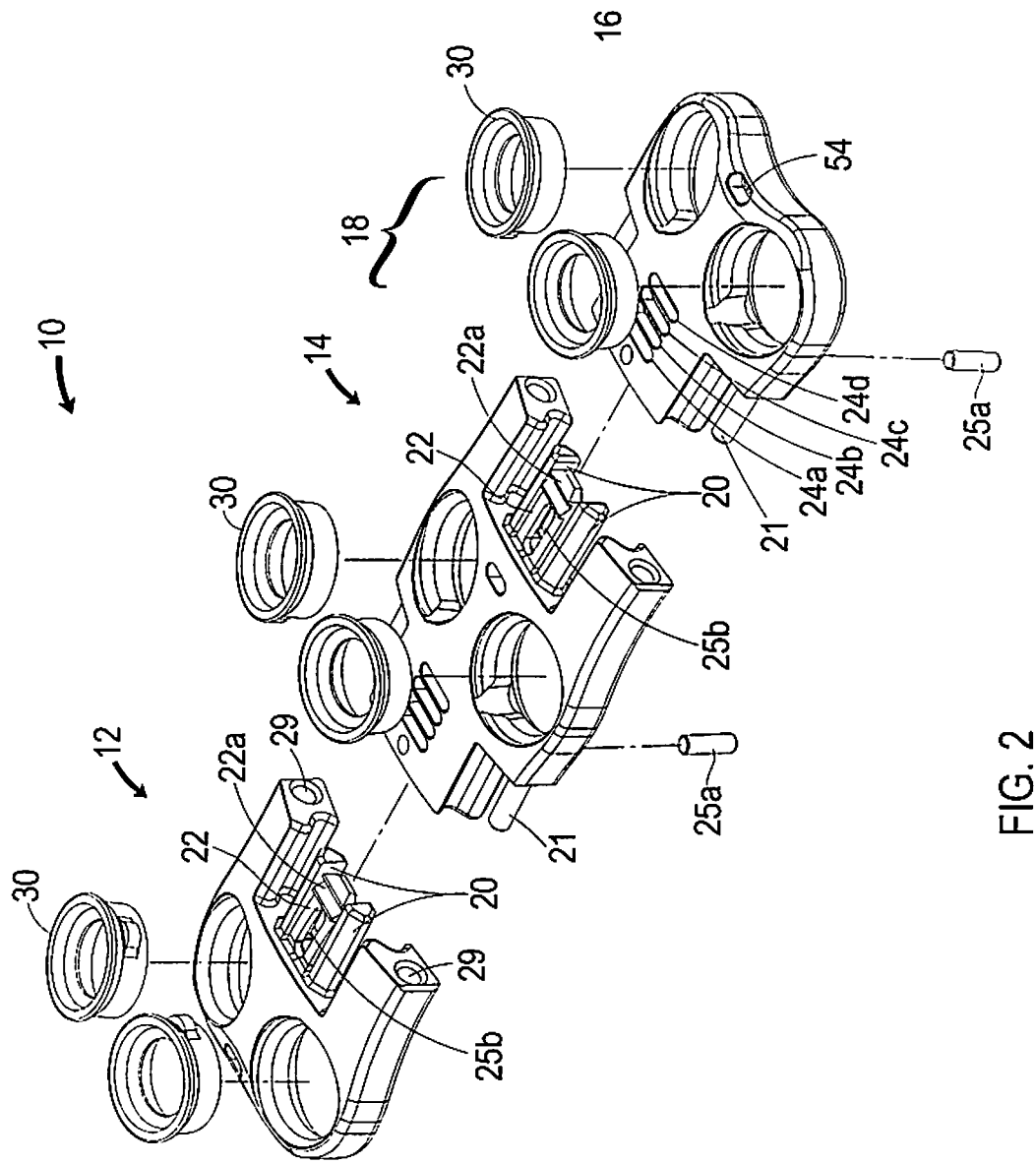
FIG. 2 is an exploded view illustrating the components of the plate shown in FIG. 1.
Figure 3:
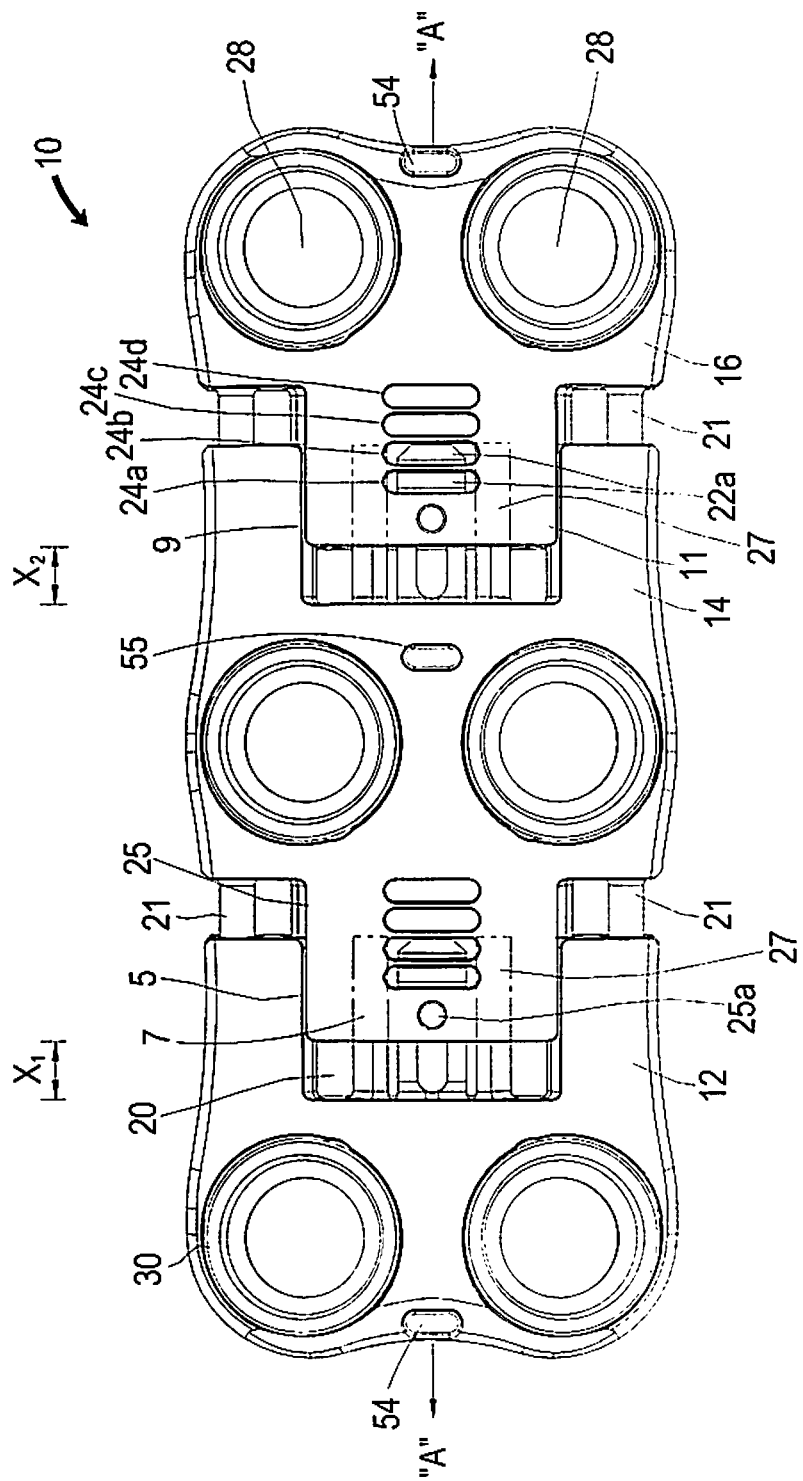
FIG. 3 is a top view of the plate shown in FIG. 1 with the segments in a spaced-apart position.

With reference to FIGS. 1 and 3, segments 12, 14, 16 of plate 10 include mating or inter-locking surfaces that fit together in a dove-tail or tongue-and-groove mechanism, allowing segments 12, 14, 16 to move or slide relative to one another along longitudinal axis "A-A" facilitates lengthening or shortening of plate 10. As will be described in detail below, a locking mechanism 18 (FIG. 2) inhibits lengthening of plate 10, but facilitates shortening of plate 10, without an additional procedure. As shown in FIG. 3, segment 12 includes a groove 5 that is shaped to receive a portion 7 of adjacent segment 14, which in turn includes a groove 9 that is shaped to receive a portion 11 of adjacent segment 16.

With additional reference to FIG. 2, one or more rails 20 extend longitudinally from the segments 12, 14 and are receivable within slots 27 of the adjacent segments 14, 16, respectively. One or more rails 21 extend longitudinally from segments 14, 16 and are receivable within slots 29 of the adjacent segments 12, 14, respectively. The length of the rails 20, 21 (as well as the length of tongue 22 and number and positioning of grooves 24a-d) determines the range within which the segments 12, 14, 16 are slidable relative to one another. Rails 20 of segment 12 are slidably received within slots 27 of segment 14; rails 20 of segment 14 are slidably received within slots 27 of segment 16; rails 21 of segment 14 are slidably received within slots 29 of segment 12; and rails 21 of segment 16 are slidably received within slots 29 of segment 14. Rails 20 have a substantially triangular cross-section and rails 21 have a circular cross-section; however, rails 20, 21 may define an alternative geometrical cross-sections, e.g., rails 20, 21 may alternatively define a square shape, an I-beam, a C-channel, or the like. Rails 20, 21 may have the same geometrical cross-section. Rails 20 may be operatively coupled to segments 12, 14 or may be an integral portion of the segments 12, 14. Rails 21 may be operatively coupled to segments 14, 16 or may be an integral portion of segments 14, 16.

Rails 20, 21 facilitate movement of segments 12, 14, 16 relative to one another along longitudinal axis "A" and stabilize plate 10 by inhibiting movement of segments 12, 14, 16 that is not along the longitudinal axis "A", e.g., rotation and/or twisting. As rails 20, 21 are inserted into slots 27, 29, as described above, locking mechanism 18 inhibits the backward movement of segments 12, 14, 16 away from one another. By inhibiting the backward movement of segments 12, 14, 16 away from one another, i.e., expansion of plate 10, the integrity and position of plate 10 is maintained while allowing compression of the anatomy, constant loading of the bone graft, and subsidence of the anatomy, which may occur over time.

Figure 4:
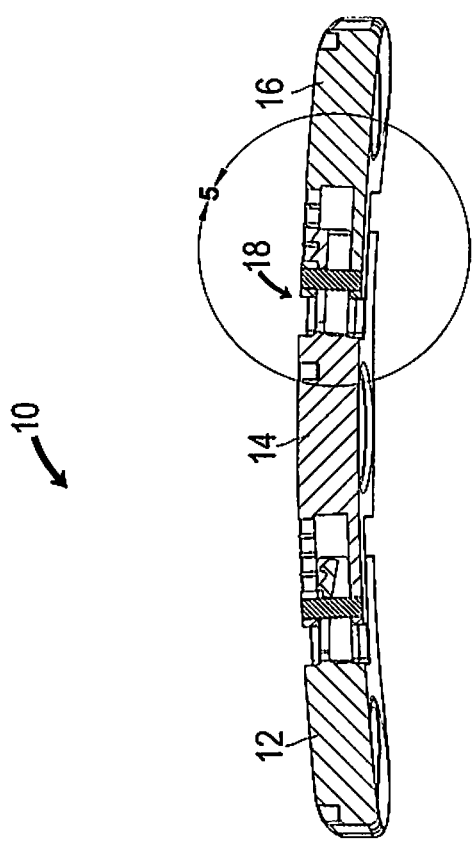
FIG. 4 is a side cross-sectional view taken along the longitudinal axis "A-A" shown in FIG. 3.
Figure 5:
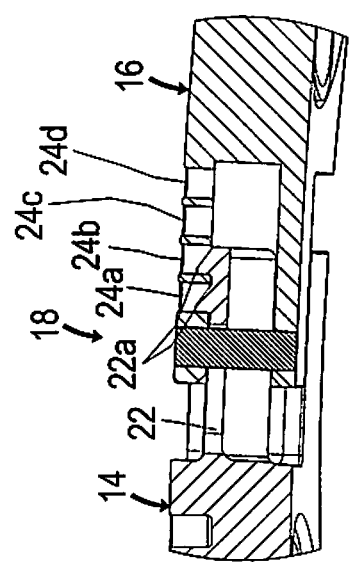
FIG. 5 is an enlargement of the detail area 5 shown in FIG. 4.

With reference to FIGS. 4 and 5, a locking mechanism 18 includes a tongue 22 and grooves 24a-d. Once rails 20, 21 couple segments 12, 14, 16 to one another there is no additional manipulation required for locking mechanism 18 to be engaged, i.e., locking mechanism 18 releasably secures segments 12, 14, 16 to each other to prevent segments 12, 14, 16 from moving apart while permitting segments 12, 14, 16 to move together. Tongues 22 of segments 12, 14 are slidably received within segments 14, 16, respectively. Rails 20, 21 facilitate sliding of tongue 22 of locking mechanism 18 to slide relatively effortlessly past the grooves 24a-d in a releasably locked engagement therewith, i.e., as tab 22a is engaged with one of grooves 24a-c. Tongue 22 may also include a guide channel 25b to receive a guide pin 25a therein to facilitate aligning of tongue 22 and to minimize off-axis movement of segments 12, 14, 16 relative to one another.

Tongue 22 includes an undercut feature or tab 22a at a distal end thereof that is configured and adapted to engage grooves 24a-d, thereby causing tongue 22 to releasably lock to one of grooves 24a-d, which are spaced at intervals or levels. As shown in FIG. 3, segment 12 and segment 14 can be maximally spaced apart by a length $x_1$, and segments 14, 16 can be maximally spaced apart by a length $x_2$. The lengths $x_1$, $x_2$ by which segments 12, 14 and segments 14, 16 are spaced, respectively, correspond to groove 24a-d to which the tab 22a of tongue 22 is releasably secured. After installation, plate 10 is able to shorten in response to subsidence without the need for a secondary operation, as segments 12, 14, 16 move together and tab 22a of tongue 22 moves into the next adjacent groove 24b-d. Grooves 24a-d can be spaced-apart at lengths or levels each representing a 1 mm reduction in lengths $x_1$, $x_2$. However, it is contemplated that each groove 24a-d can be spaced-apart at a length greater or less than 1 mm. It has been shown that when grooves 24a-d are spaced-apart at a length of 1 mm, optimal compression is maintained on an implant positioned between adjacent vertebrae promoting fusion of the vertebrae and the implant.

The interaction of tab 22a with grooves 24 allows segments 12, 14, 16 to move closer together but not apart, i.e., once one of grooves 24 engages tab 22a, movement of segments 12, 14, 16 apart is inhibited. The shape of tab 22a allows tab 22a to disengage groove 24 in a direction that will move segments 12, 14, 16 together, but not in a direction that would move or distract segments 12, 14, 16 apart without requiring an additional, secondary user operation. It is desirable to maintain loading on the vertebral bodies to help maintain a graft and/or implant in position until fusion is completed to facilitate the healing process. Inhibiting segments 12, 14, 16 of plate 10 from moving or distracting apart from each other aids in the healing process by maintaining loading on the vertebrae.

Referring to FIGS. 1-1A, segments 12, 14, 16 of plate 10 can include a first compression notch 54 and a second compression notch 55. Compression notches 54, 55 are configured to cooperate with locking mechanism 18 to compress lengths $x_1$, $x_2$ after bone screws 40 attach plate 10 to vertebrae such that a compression force or preload is applied to the space between vertebrae engaged by segments 12, 14, 16 of plate 10. First compression notch 54 is positioned adjacent to and spaced apart from the outer edges (top and bottom edges when plate 10 is attached to vertebrae) of segments 12 and 16 as shown in FIGS. 1 and 3. As shown, the compression notches 54 are placed at or near the lateral mid-point of the plate segment 12, 14, 16, with the screw holes 28 disposed laterally outward of the axis between the notches 54 and 55.

With reference to FIGS. 1A and 2, plate 10 includes screw holes 28 adapted for the reception of bone screws 40 therethrough. An insert 30 may be press-fitted into each screw hole 28. In an embodiment, inserts 30 may be removable. Inserts 30 may be formed from a material that is softer than that forming the bone screws 40. For example, the insert 30 may be formed from commercially pure implant grade titanium. An inward facing lip (not shown) is configured and adapted to engage threads 41 of bone screw 40. The harder material, e.g., implant grade titanium alloy, of bone screw 40 deforms the softer material, e.g., commercially pure titanium, forming the lip of insert 30. This engagement inhibits the screw from migrating out of plate 10, as well as the bone, as is described in U.S. Pat. Nos. 8,449,585 and 6,322,562, both of which are incorporated herein by reference. Although plate 10 is shown as having screw holes 28, it is contemplated that a plate may be used that lacks holes 28. For example, a plate may be attached to a bone by using screws that are self-starting or self-tapping or drills may be used to prepare holes within a plate for screws.

Other structures for locking screws to plates are known and can be used. In addition, inserts 30, although shown and described as being part of plate 10, may be used with a static plate that does not include movable or adjustable segments. Inserts 30 when used with a bone plate, whether adjustable or static, would provide enhanced screw retention within the screw holes of such plates.

As described, screws 40 may be formed from a biocompatible material. By way of example, plate 10 may be formed from a PEEK or titanium alloy, inserts 30 formed from commercially pure implant grade titanium, and screws 40 formed from a titanium alloy. The use of materials having different characteristics, such as different hardness, facilitates screw-plate engagement, and inhibits screw back out.

Plate 10, locking mechanism 18, and rails 20, 21 can be made from a relatively hard material, e.g., implant grade titanium alloy, and inserts 30 are made from a relatively softer material, e.g., commercially pure implant grade titanium. In another embodiment, plate 10 and/or rails 20, 21 may be made of another implant grade material, such as, but not limited to, commercially pure titanium, titanium alloys, cobalt chrome alloys, PEEK, and the like.

Figure 6:
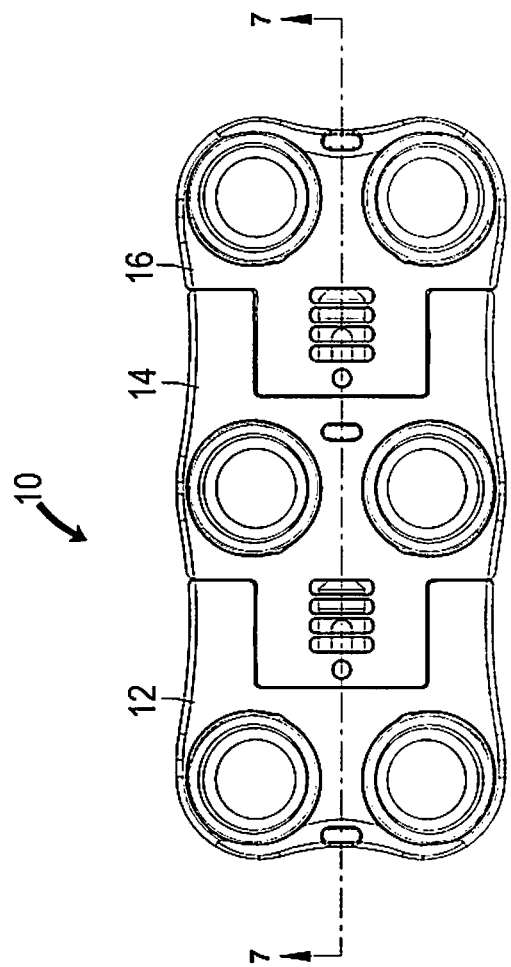
FIG. 6 is a top view of the plate shown in FIG. 1 with the segments in a compressed position.
Figure 7:
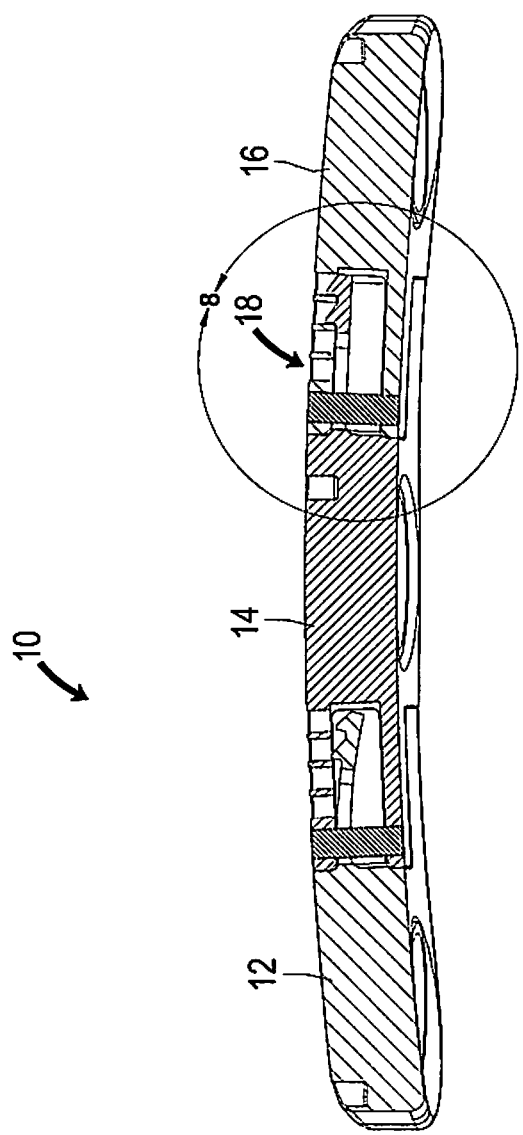
FIG. 7 is a cross-sectional view taken along the line "7-7" shown in FIG. 6.
Figure 8:
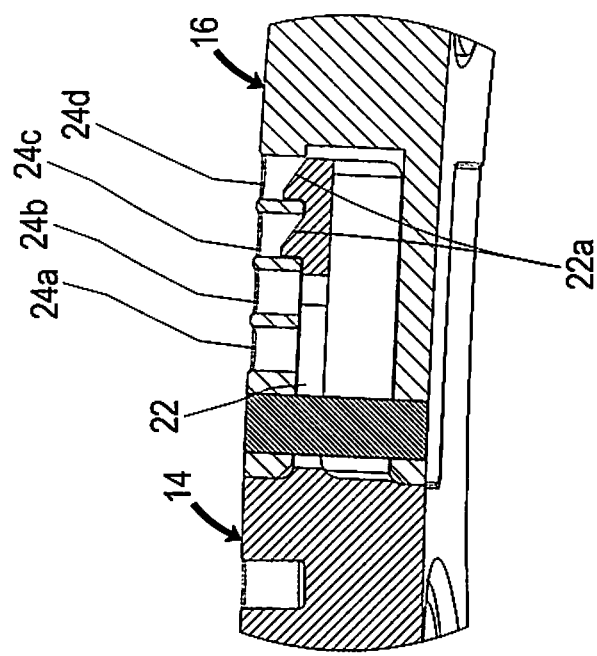
FIG. 8 is an enlargement of the detail area 8 shown in FIG. 7.

Referring to FIGS. 4-8, segments 12, 14, 16 of plate 10 may be maximally spaced apart thereby facilitating the greatest degree of adjustment to fit the anatomy of the patient as shown in FIGS. 4 and 5. Tab 22a of tongue 22 may be received within the outward most groove 24a such that segments 12, 14, 16 are maximally spaced apart, but are inhibited from moving apart from one another without a secondary user operation to disengage tab 22a from groove 24a. Plate 10 is placed onto the vertebral bodies such that screw holes 28 are located on the anterior portion of the most cranial vertebral body. Screws 40 (FIG. 1A) are placed into the two most cranial screw holes 28 to anchor plate 10 in place. The next adjacent segment is adjusted to align holes 28 with the next vertebral body so that screws 40 can be inserted through holes 28 and into the vertebral body. This process is repeated for each additional vertebral segment. As shown in FIGS. 6-8, segments 12, 14, 16 of plate 10 are in a minimally spaced apart or compressed position with tab 22a engaging groove 24d.

A standard plate holder (not shown) can be used to facilitate placement of plate 10 and holding of plate 10 during insertion of the screw 40. In addition, a compression instrument 60 (FIG. 9) may be used to help expand or contract the adjacent segments 12, 14, 16 as described in detail below. Removable spacers or wedges 90 (FIG. 1A) may hold segments 12, 14, 16 in a predetermined spaced orientation during implantation by being positioned between segments 12, 14, 16 and impeding movement of segments 12, 14, 16 toward one another in a predetermined spaced orientation during the implantation of plate 10. Removable wedges 90 can be positioned over and configured to engage rails 21 between segments 12, 14, 16. After implantation of plate 10, removable wedges 90 are removed from the plate 10, thereby permitting segments 12, 14, 16 to move relative to one another. It will be appreciated that removable wedges 90 are removed before a compression instrument is used to compress or preload plate 10 as described in detail below. It is envisioned that wedges 90 are usable with all disclosed embodiments of the plate.

Figure 9:
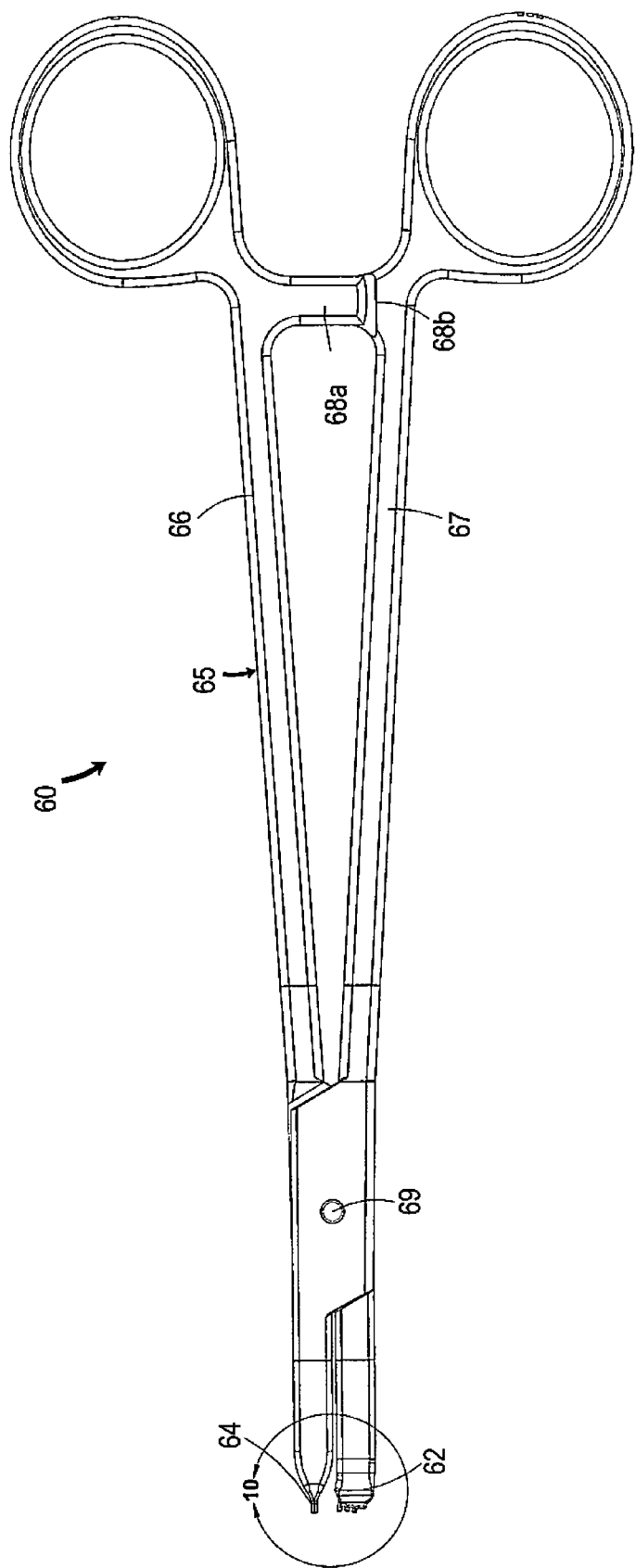
FIG. 9 is a side view of an exemplary embodiment of a compressor instrument in accordance with the present disclosure.
Figure 10A:
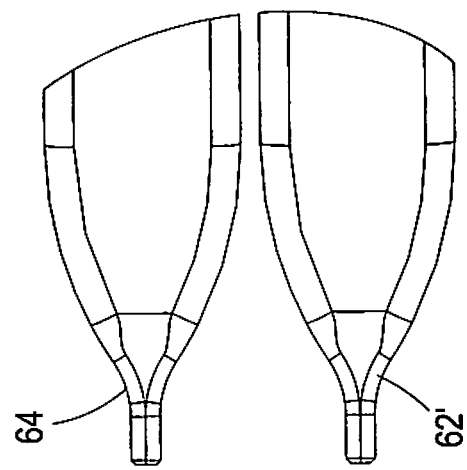
FIG. 10A is a enlarged side view of another exemplary embodiment of the tips of a compressor instrument in accordance with the present disclosure.
Figure 10:
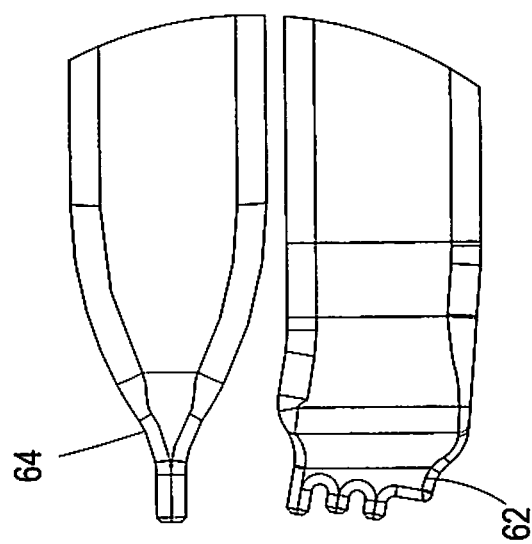
FIG. 10 is an enlargement of the detail area 10 shown in FIG. 9.

Referring to FIGS. 9-10A, a compression instrument 60 is sized and configured to engage plate 10. Compression instrument 60 includes a first tip 62, a second tip 64, and a handle 65. First tip 62 is sized and configured to engage grooves 24a-d of plate 10 and second tip 64 is sized and configured to engage compression notches 54 of plate 10 of adjacent segments. In embodiments, first tip 62 can include more than one protrusion each configured to engage adjacent grooves 24a-d. In some embodiments, first tip 62' includes a protrusion configured to engage a suitable structure, e.g., notches 54, 55, grooves 24a-d, etc., on one segment 12, 14, 16 and second tip 64 is configured to engage a suitable structure, e.g., notches 54, 55, grooves 24a-d, etc., on an adjacent segment 12, 14, 16. First and second tips 62, 64 are moveable relative to one another. Handle 65 is operatively associated with first and second tips 62, 64 to move tips 62, 64 relative to one another. Handle 65 can have a first arm 66 operatively associated with first tip 62 and a second arm 67 operatively associated with second tip 64. First and second arms 66, 67 can pivot about a pivot pin 69 to move tips relative to one another. Handle 65 can include clamping members 68a, 68b positioned on first and second arms 66, 67 respectively. Clamping members 68a, 68b can each have ridges that engage ridges on the opposing clamping member 68a, 68b such that as first and second arms 66, 67 are moved towards each other, clamping members 68a, 68b provide tactile feedback of each level of compression.

Figure 11:
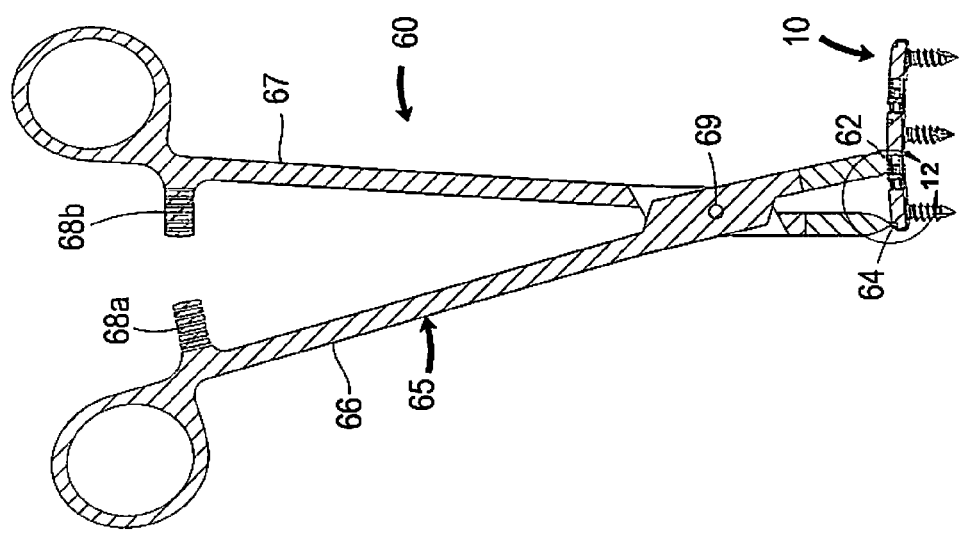
FIG. 11 is a cross-sectional view taken along the longitudinal axis of the plate shown in FIG. 1 engaged with the compressor instrument of FIG. 9.
Figure 12:
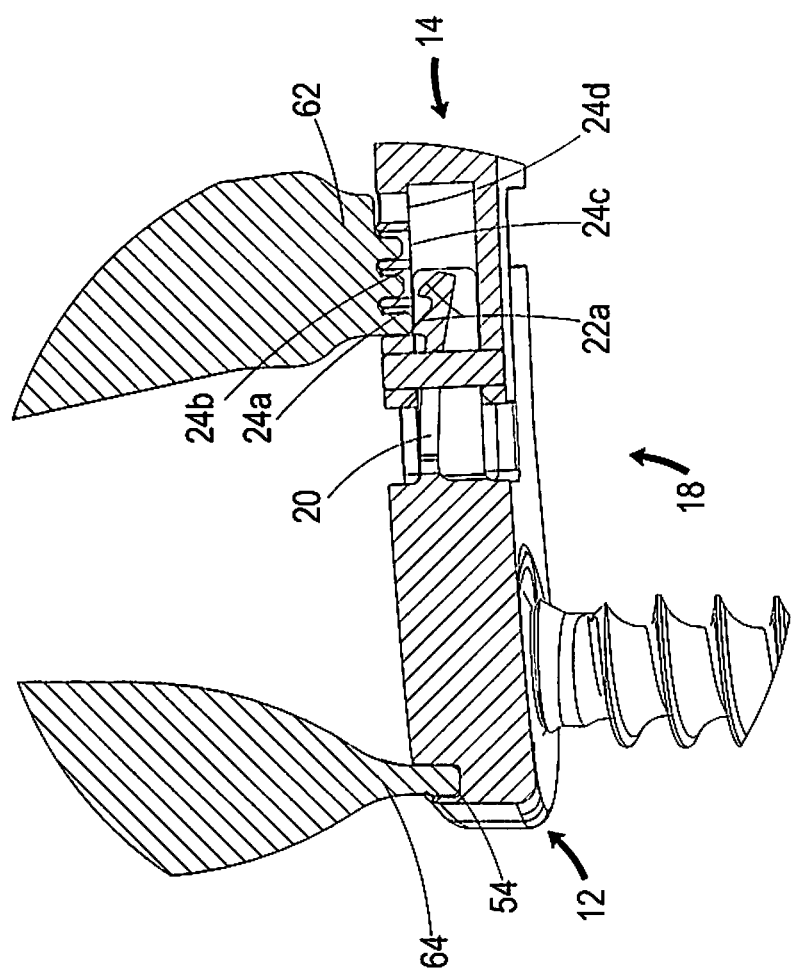
FIG. 12 is an enlargement of the detail area 12 shown in FIG. 11.

With reference to FIGS. 11 and 12, compression instrument 60 engages locking mechanism 18 of segments 12 and 14. First tip 62 of compression instrument 60 is inserted into grooves 22a-d of locking mechanism 18 of segment 14 and second tip 64 of compression instrument 60 is inserted into first compression notch 54 of segment 12. In some embodiments, first tip 62 disengages tab 22a of tongue 22 from grooves 24a-d when inserted into grooves 24a-d. Handle 65 is manipulated to move tips 62, 64 towards one another such that segments 12 and 14 are moved towards the compressed position such that a preload or compression force is applied to the vertebrae engaged by segments 12 and 14 of plate 10. Tab 22a and/or clamping members 68a, 68b can provide tactile feedback for each level of compression applied to segments 12, 14. It will be appreciated that compression can be applied to each set of adjacent segments 12, 14, 16 of plate 10. For example, to compress adjacent segments 14 and 16, first tip 62 can be inserted in grooves 24a-4 of segment 16 and second tip 64 is inserted in second compression notch 55 of segment 14.

In embodiments where first tip 62 disengages tab 22a from grooves 24a-d, compression instrument 60 can release locking mechanism 18 allowing the segments 12, 14, 16 to move apart from one another to allow for surgical adjustment.

Figure 13:
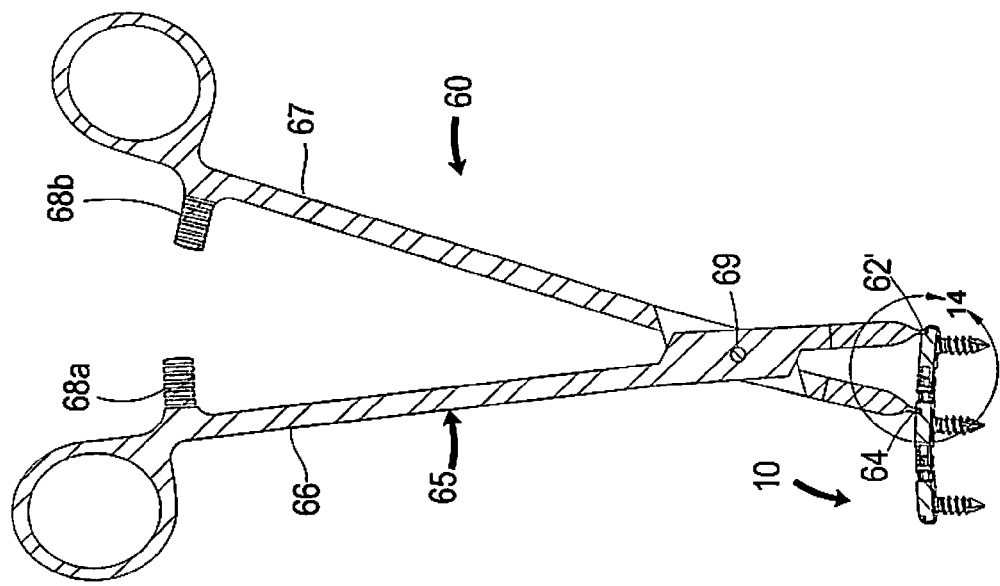
FIG. 13 is a cross-sectional view taken along the longitudinal axis of the plate shown in FIG. 1 engaged with a compressor instrument including the tips shown in FIG. 10A.
Figure 14:
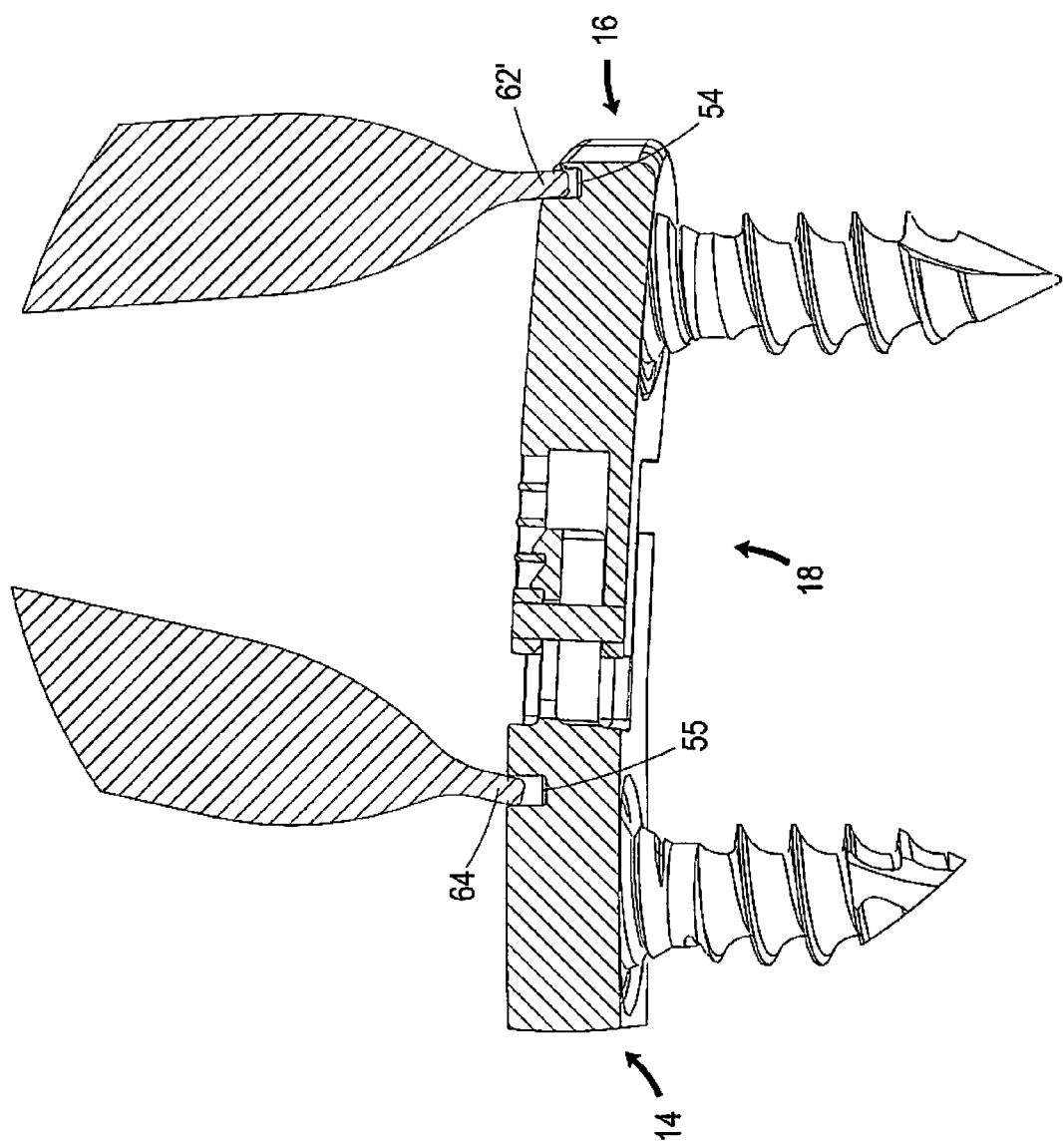
FIG. 14 is an enlargement of the detail area 14 shown in FIG. 13.

With reference to FIGS. 13 and 14, compression instrument 60 engages locking mechanism 18 of segments 14 and 16. First tip 62' of compression instrument 60 is inserted in first compression notch 54 of segment 16 and second tip 64 of compression instrument 60 is inserted into second compression notch 55 of segment 14. Handle 65 is manipulated to move tips 62', 64 towards one another such that segments 14 and 16 are moved towards the compressed position such that a preload or compression force is applied to the vertebrae engaged by segments 14 and 16 of plate 10. Tab 22a and/or clamping members 68a, 68b can provide tactile feedback for each level of compression applied to segments 14, 16. It will be appreciated that compression can be applied to each set of adjacent segments 12, 14, 16 of plate 10. In particular, compression will be applied to an adjacent pair of segments and the instrument will be repositioned to apply compression to a different pair of adjacent segments.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method of attaching a bone plate to vertebrae, the method comprising:
    providing a bone plate including:
        a first segment having a first compression notch and a first screw hole;
        a second segment defining a second screw hole and defining a second compression notch in a top surface thereof, the first and second segments positioned along a longitudinal axis and movable relative to one another; and
        a locking mechanism inhibiting relative axial movement of the first and second segments away from one another along the longitudinal axis, the locking mechanism having first and second grooves disposed on the second segment, the locking mechanism including a tongue extending from the first segment;
    securing the first segment of the bone plate to a first vertebra with a first bone screw inserted through the first screw hole;
    securing the second segment of the bone plate to a second vertebra with a second bone screw inserted through the second screw hole;
    inserting a first tip of a compression instrument in the first and second grooves and inserting a second tip of the compression instrument in the first compression notch; and
    compressing the first segment of the bone plate towards the second segment of the bone plate with the compression instrument, the tongue engaging the first and second grooves to sequentially and releasably lock the first and second segments, thereby inhibiting axial movement of the first and second segments apart from one another while enabling axial movement of the first and second segments towards one another.

2. The method according to claim 1, wherein compressing the first segment of the bone plate towards the second segment of the bone plate includes compressing a handle of the compression instrument.

3. The method according to claim 1, further comprising translating the first segment away from the second segment with the compression instrument.

4. The method according to claim 3, wherein translating the first segment away from the second segment with the compression instrument includes engaging the tongue with the first tip, and separating the first and second tips of the compression instrument.

5. The method according to claim 4, wherein engaging the tongue with the first tip disengages the tongue from the first and second grooves.

6. The method according to claim 4, wherein separating the first and second tips of the compression instrument includes moving first and second arms of the compression instrument away from one another.

7. The method according to claim 1, further comprising permitting the first and second segments to move towards one another in response to subsidence of the first and second vertebrae.

8. The method according to claim 1, further comprising removing a spacer positioned between the first and second segments of the bone plate before compressing the first segment of the bone plate towards the second segment of the bone plate, the spacer maintaining a predefined space between the first and second segments.

9. A method of attaching a bone plate to vertebrae, the method comprising:
securing a first segment of a bone plate to a first vertebra with a first bone screw inserted through a first screw hole defined through the first segment;
securing a second segment of the bone plate to a second vertebra with a second bone screw inserted through a second screw hole defined through the second segment;
inserting a first tip of a compression instrument in first and second grooves disposed on the second segment; and
compressing the first segment of the bone plate towards the second segment of the bone plate with the compression instrument, a tongue extending from the first segment engages the first and second grooves to sequentially and releasably lock the first and second segments, thereby inhibiting axial movement of the first and second segments apart from one another while enabling axial movement of the first and second segments towards one another.

10. The method according to claim 9, wherein compressing the first segment of the bone plate towards the second segment of the bone plate includes compressing a handle of the compression instrument while the first tip of the compression instrument is inserted in the first and second grooves and a second tip of the compression instrument engages a first compression notch defined in the first segment.

11. The method according to claim 9, further translating the first segment away from the second segment with the compression instrument.

12. The method according to claim 11, wherein translating the first segment away from the second segment with the compression instrument includes engaging the first compression notch with a second tip of the compression instrument, and wherein inserting the first tip of the compression instrument in the first and second grooves includes inserting the first tip through at least one of the first and second grooves to engage the tongue, and separating the first and second tips of the compression instrument.

13. The method according to claim 12, wherein inserting the first tip of the compression instrument through the at least one of the first and second grooves to engage the tongue disengages the tongue from the first and second grooves.

14. The method according to claim 12, wherein separating the first and second tips of the compression instrument includes moving first and second arms of the compression instrument away from one another.

15. The method according to claim 11, further comprising permitting the first and second segments to move towards one another in response to subsidence of the first and second vertebrae.

16. The method according to claim 11, further comprising removing a spacer positioned between the first and second segments of the bone plate before compressing the first segment of the bone plate towards the second segment of the bone plate, the spacer maintaining a predefined space between the first and second segments.

* * * * *